(12) United States Patent
Rezach et al.

(10) Patent No.: US 8,888,821 B2
(45) Date of Patent: Nov. 18, 2014

(54) SPINAL IMPLANT MEASURING SYSTEM AND METHOD

(75) Inventors: William Alan Rezach, Atoka, TN (US); Rodney Ballard, Lakeland, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 23 days.

(21) Appl. No.: 13/440,700

(22) Filed: Apr. 5, 2012

(65) Prior Publication Data
US 2013/0268007 A1 Oct. 10, 2013

(51) Int. Cl.
*A61B 17/88* (2006.01)
(52) U.S. Cl.
USPC ............ 606/279; 606/86 A; 606/99; 606/102
(58) Field of Classification Search
USPC .................... 606/86 A, 96, 99, 102, 129, 279
See application file for complete search history.

(56) References Cited

U.S. PATENT DOCUMENTS

| 2007/0073293 A1* | 3/2007 | Martz et al. ............. 606/61 |
| 2010/0191088 A1* | 7/2010 | Anderson et al. ............. 600/373 |
| 2013/0079792 A1* | 3/2013 | Stein et al. ............. 606/102 |

* cited by examiner

*Primary Examiner* — Mary Hoffman
*Assistant Examiner* — Christina Negrellirodrigue

(57) ABSTRACT

A method for measuring a spinal implant comprises the steps of: providing a device including a gauge configured to measure an angle in a measuring plane and extending to an engagement surface; disposing the engagement surface with a first selected position of an implant or an anatomy, the first selected position being disposed at a first orientation; calibrating the gauge to a zero angle measurement at the first orientation; disposing the engagement surface with a second selected position of the implant or the anatomy, the second selected position being disposed at a second orientation; and measuring an angle of the second orientation relative to the first orientation such that the gauge determines the angle relative to the zero angle measurement. Various devices are disclosed.

16 Claims, 5 Drawing Sheets

SPINAL IMPLANT MEASURING SYSTEM AND METHOD

TECHNICAL FIELD

The present disclosure generally relates to medical devices, systems and methods for the treatment of musculoskeletal disorders, and more particularly to systems and methods for determining geometries of a spinal implant, and in particular a spinal rod.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatments of these spinal disorders include discectomy, laminectomy, fusion and implantable prosthetics. During surgical treatment, one or more rods may be attached via fasteners to the exterior of two or more vertebral members in a vertebral fixation system. When a rod is positioned within a fixation system, the rod may require bending and shaping to conform to a curvature of a spine of a patient. This disclosure describes an improvement over these prior art technologies.

SUMMARY

Accordingly, a method for measuring a spinal implant is provided. The method comprises the steps of: providing a device including a gauge configured to measure an angle in a measuring plane and extending to an engagement surface; disposing the engagement surface with a first selected position of an implant or an anatomy, the first selected position being disposed at a first orientation; calibrating the gauge to a zero angle measurement at the first orientation; disposing the engagement surface with a second selected position of the implant or the anatomy, the second selected position being disposed at a second orientation; and measuring an angle of the second orientation relative to the first orientation such that the gauge determines the angle relative to the zero angle measurement.

In one embodiment, a method for measuring a spinal implant geometry is provided. The method comprising the steps of: surgically treating a spine disorder including connecting a spinal rod at an interface with vertebrae in a predetermined orientation; providing a gauge extending to an engagement surface, the engagement surface defining an implant cavity configured for disposal of the spinal rod; disposing the engagement surface with a first selected position of the spinal rod such that the spinal rod is disposed in the implant cavity, the first selected position being disposed at a first orientation of the spinal rod; calibrating the gauge to a zero angle measurement at the first orientation; disposing the engagement surface with a second selected position of the spinal rod such that the spinal rod is disposed in the implant cavity, the second selected position being disposed at a second orientation of the spinal rod; measuring an angle of the second orientation relative to the first orientation such that the gauge determines the angle relative to the zero angle measurement; adjusting the spinal rod based on the comparison of the angle to the predetermined orientation.

In one embodiment, a device for measuring a spinal rod implant is provided. The device comprises a gauge having an electrical circuit configured to measure an angle in a measuring plane. The gauge is coupled to a shaft that extends to an end portion. An engagement surface is disposed with the end portion and parallel to the measuring plane of the gauge. The engagement surface defines an implant cavity configured to receive a portion of a spinal implant at a first selected position of the spinal implant such that the gauge is calibrated to a zero angle measurement and at a second selected position of the spinal implant such that the gauge measures an angle of the first selected position relative to the second selected position to determine the angle relative to the zero angle measurement.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
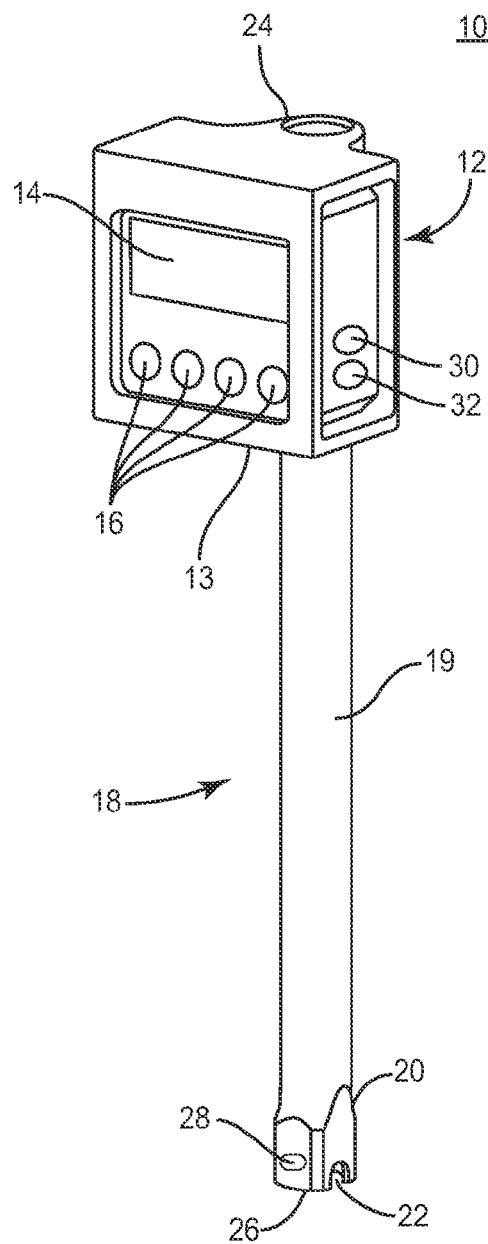
FIG. 1 is a perspective view of one embodiment of a system for measuring a spinal implant in accordance with the principles of the present disclosure.

The exemplary embodiments of the system and method for measuring a surgical spinal implant are discussed in terms of medical devices for the treatment of musculoskeletal disorders and more particularly, in terms of a measurement system that measures the configuration and/or geometry of an implant, such as, for example, a spinal rod used to treat a musculoskeletal system, such as, for example, the spine of a patient. It is envisioned that the system may be configured to measure angular geometry and/or position of an implant employed for stabilization of a vertebral column. It is further contemplated that the system may be configured to collect data from spinal implants and/or anatomy regarding geometry and/or position relative to other portions of an implant, other implants and/or anatomy.

It is envisioned that the present disclosure may include reading angular position during spine surgery. It is further envisioned that a method of employing the disclosed system may include engaging a device with an implant, such as, for example, a spinal rod or engaging the anatomy of a patient being treated. The device may include a gauge that is disposed at a first position of an implant, such as, for example, a spinal rod and/or the anatomy of a patient to calibrate the device, for example, to a zero angle reading. For example, the zero angle reading can zero out the device. The device may repositioned to a second position on the implant and/or the anatomy of a patient to measure an angle relative to the zero angle reading position and output the angular measurement between the first and second positions. It is envisioned that the angular measurement may be output via visual and/or audible indicia.

It is contemplated that a medical practitioner may manually manipulate the anatomy of a patient, such as, for example, a spine of a patient to a selected orientation such that the system of the present disclosure measures the angular difference between a first selected position and a first selected orientation; and a second selected position and a second selected orientation. It is further contemplated that the system and method of the present disclosure can be used for determining sagittal alignment during a pedicle subtraction osteotomy procedure (PSO).

It is envisioned that the system and method of the present disclosure may be employed to verify the contour of a spinal implant, such as, for example, a spinal rod. Such verification of contour can be performed during a surgical procedure in situ or out of a body, such as, for example, on a back table in an operating room. It is contemplated that the system and method of the present disclosure may be employed to verify sagittal balance with regard to an implant/spinal rod interface and/or measure the amount of correction achieved during a trauma procedure.

The system and method of the present disclosure may be employed to verify the amount of axial derotation and may be adapted to engage a surgical instrument, such as, for example, a surgical extender and measure the amount of axial derotation achieved. It is envisioned that the system can be attached to an apex of a scoliosis curve to measure the amount of manual derotation applied within an axial plane. It is further envisioned that the system can be employed to measure a series of vertebral levels, multiple vertebral levels, vertebral level to vertebral level and/or a single vertebral level. It is contemplated that the system can measure an implant interface angle between specific vertebrae such as, for example, the device can measure the angular relationship between the L5 vertebra and L1 vertebra.

It is envisioned that the system and method of the present disclosure may include and/or attach to a surgical instrument, such as, for example, a counter torque instrument and/or a rod gripper instrument to measure the angle between the instrument and another device, implant or the anatomy of a patient and/or the angle between a first portion of the device or implant and a second portion of the same device or implant.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is contemplated that the disclosed systems and methods may be alternatively employed in a surgical treatment with a patient in a prone or supine position, and/or employ various surgical approaches to the spine, including anterior, posterior, posterior mid-line, medial, lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "superior" and "inferior" are relative and used only in the context to the other, and are not necessarily "upper" and "lower".

Further, as used in the specification and including the appended claims, "treating" or "treatment" of a disease or condition refers to performing a procedure that may include administering one or more drugs to a patient in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications in the described devices, instruments, methods, and any further application of the principles of the disclosure as described herein are contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. The following discussion includes a description of a surgical implant measuring system and related methods in accordance with the principles of the present disclosure. Alternate embodiments are also disclosed. Reference will now be made in detail to the exemplary embodiments of the present disclosure, which are illustrated in the accompanying figures. Turning now to FIG. 1, there are illustrated components of a surgical implant measuring system, such as, for example, an angle gauge measurement system 10 in accordance with the principles of the present disclosure.

The components of system 10 can be fabricated from biologically acceptable materials suitable for medical applications, including metals, synthetic polymers, ceramics and bone material and/or their composites, depending on the particular application and/or preference of a medical practitioner. For example, the components of system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 10 may have material composites, including the above materials, to achieve various desired characteristics such as strength, rigidity, elasticity, compliance, biomechanical performance, durability and radiolucency or imaging preference. The components of system 10, individually or collectively, may also be fabricated from a heterogeneous material such as a combination of two or more of the above-described materials. The components of system 10 may be monolithically formed, integrally connected or include fastening elements and/or instruments, as described herein.

Angle gauge measurement system 10 includes a device 12. Device 12 includes a box or housing used to enclose components of system 10, such as, for example, a gauge (not shown) having an electrical circuit configured to measure an angle in a measuring plane. Device 12 is substantially hollow and has a rectangular configuration. It is envisioned that device 12 may be variously configured and dimensioned, such as, for example, round, oval, oblong, square, rectangular, polygonal and/or solid depending on the requirements of a particular application. It is further envisioned that device 12 may be sealed, such as, for example, to prevent passage of gas and/or fluid from entering device 12 to protect components within an interior portion of device 12 from exposure to liquid, gas or other materials.

The gauge may include a circuit or integrated circuit device such as, for example, one or more accelerometers, rotary capacitive sensors, a solid-state sensor incorporating an accelerometer or a potentiometer, solid-state sensors employing other physical properties (e.g., a magnetic field sensor or other device the employs magneto resistance), or any other mechanical or electronic device that measures an angle in a measuring plane relative to a defined reference. It is envisioned that the gauge may include a bubble system, a pendulum system, a coil system or any other device or mechanism that accurately measures an angle in a measuring plane.

A probe 18 is coupled to device 12. Probe 18 has a shaft 19 extending from device 12. Probe 18 has an end portion 20 opposite the gauge enclosed within device 12. Shaft 19 has a substantially cylindrical configuration and has a maximum width or diameter that is less than a maximum width or diameter of device 12. Shaft 19 can include an inner surface defining a longitudinal passageway extending through all or only a portion of shaft 19. It is envisioned that shaft 19 may have alternate cross section configurations, such as, for example, oval, oblong, triangular, square, polygonal, irregular, uniform, non-uniform, offset, staggered, undulating, arcuate, variable and/or tapered a removable gauge. In one embodiment, device 12 and/or the gauge supported therewith is removably connected with probe 18. For example, the device 12 and/or the gauge may be connected and disconnected with probe 18 for attachment with other probes, shafts and/or surgical instruments. It is contemplated that device 12 and/or the gauge may be removable with probe 18 via a clip, keyed geometry and/or threaded connection. In one embodiment, device 12 and/or the gauge may be permanently affixed to probe 18.

Device 12 includes an aperture 24 configured for disposal of shaft 19 to retain device 12 with probe 18. Shaft 19 may be removably disposed within aperture 24 or may be permanently fixed within aperture 24, depending on the requirements of a particular application. A length of shaft 19 may be selectively adjusted by sliding a portion of its length into aperture 24 and securing probe 18 at a desired length. It is envisioned that shaft 19 may include one or more overlapping sections, such as, for example, a telescopic configuration such that shaft 19 can selectively adjust the length of shaft 19 without adjusting the length of shaft 19 disposed in aperture 24. Aperture 24 may be configured with a slot, a flat or other indexing structure to prevent rotation of probe 18 about its longitudinal axis. It is envisioned that at least a portion of shaft 19 and aperture 24 may be threaded such that the threads on shaft 19 engage the threads on aperture 24 to retain device 12 with probe 18. It is further envisioned that probe 18 may be retained with device 12 in alternative fixation configurations, such as, for example, friction fit, pressure fit, locking protrusion/recess, locking keyway and/or adhesive.

An end portion 20 of probe 18 includes an engagement end or surface 26 defining an implant cavity 22. Engagement surface 26 is parallel to a measuring plane of the gauge. Implant cavity 22 is a U-shaped channel that extends transversely across engagement surface 26 and includes an axially facing opening configured to receive a spinal implant, such as, for example, a spinal rod for measuring an angle of the rod relative to another portion of the rod, a separate implant and/or the anatomy of a patient. It is envisioned that cavity 22 may be variously configured and dimensioned, such as, for example, oval, oblong, triangular, square, polygonal, irregular, uniform, non-uniform, offset, staggered, undulating, arcuate, variable, planar, concave, convex, polygonal, irregular, uniform, non-uniform, staggered, tapered, consistent or variable, depending on the requirements of a particular application.

Figure 3:
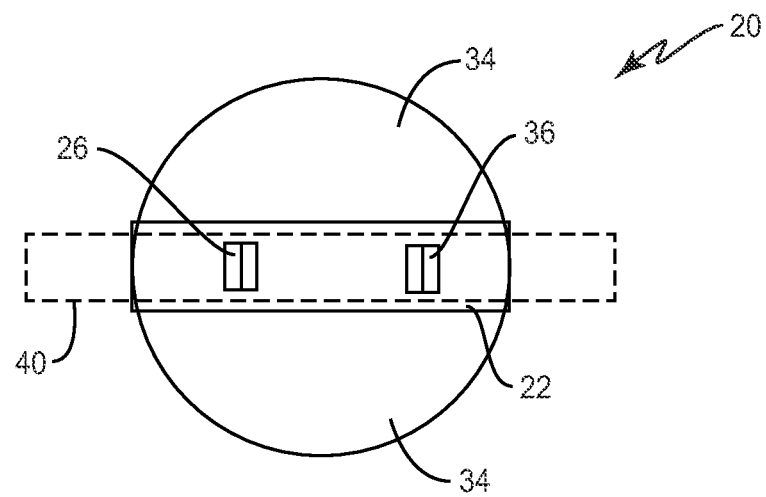
FIG. 3 is an end view of an end portion of a component of the system shown in FIG. 1.

Engagement surface 26 may also include surfaces adjacent to cavity 22, which may be configured to and employed for engaging probe 18 with various anatomical surfaces, such as, surfaces of bones and surfaces of vertebrae. End portion 20 includes surfaces 34, as shown in FIG. 3, which may be employed for taking angular measurements against a surface, such as, for example, a spinal rod 40 or anatomy of a patient. Cavity 22 may include one or a plurality of engagement points 36 to provide at least one stable point on which an implant, such as, for example, spinal rod 40 can make contact during a measurement. Engagement points 36 improve the repeatability and reliability of the angle measurements and are spaced apart from one another to enable the angular measurement.

End portion 20 includes a tracking element, such as, for example, a position sensor 28 configured to identify a position of device 12. Sensor 28 may be utilized in connection with a computer or other device to send and receive data between device 12 and the computer or other device. The position of device 12 may optionally be obtained concurrently with an angular measurement and the position and the angular measurement may be relayed to a computer or other device for storage and analysis. Sensor 28 may be placed at a position corresponding to a contact area where a measurement is made, such as, for example, on end portion 20.

In one embodiment, system 10 includes a surgical tracking system. In one embodiment, the system 10 includes an optical tracking system, an electromagnetic tracking system, an acoustic tracking system, an ultrasound tracking system and/or an active device tracking system. In one embodiment, the tracking system uses a sensor or coil in wireless communication with a detector to determine position and rotation data of the probe. For example, probe 18 has an active internal guidance system can include gyroscopes and/or accelerators that can be used to track the position and rotation of probe 18 during its operation and be in direct communication with the control computer or processor, without the need for the detector. Probe 18 can communicate positional and rotational information of probe 18 to the processor in either a wired or wireless configuration. It is envisioned that tracking is relative to a spinal implant and that no wider coordinate system may be required.

In one embodiment, device 12 includes a communication system with a computer or network using wireless or wired methods to remotely collect, store and/or analyze the data measured by the device 12. Device 12 may include a receiver 30 and a transmitter 32 for communication with an external computer or network. It is envisioned that device 12 store and analyze data within device 12 via a memory and a processor for example, which would obviate the need for a computer which is separate from device 12.

Figure 5:
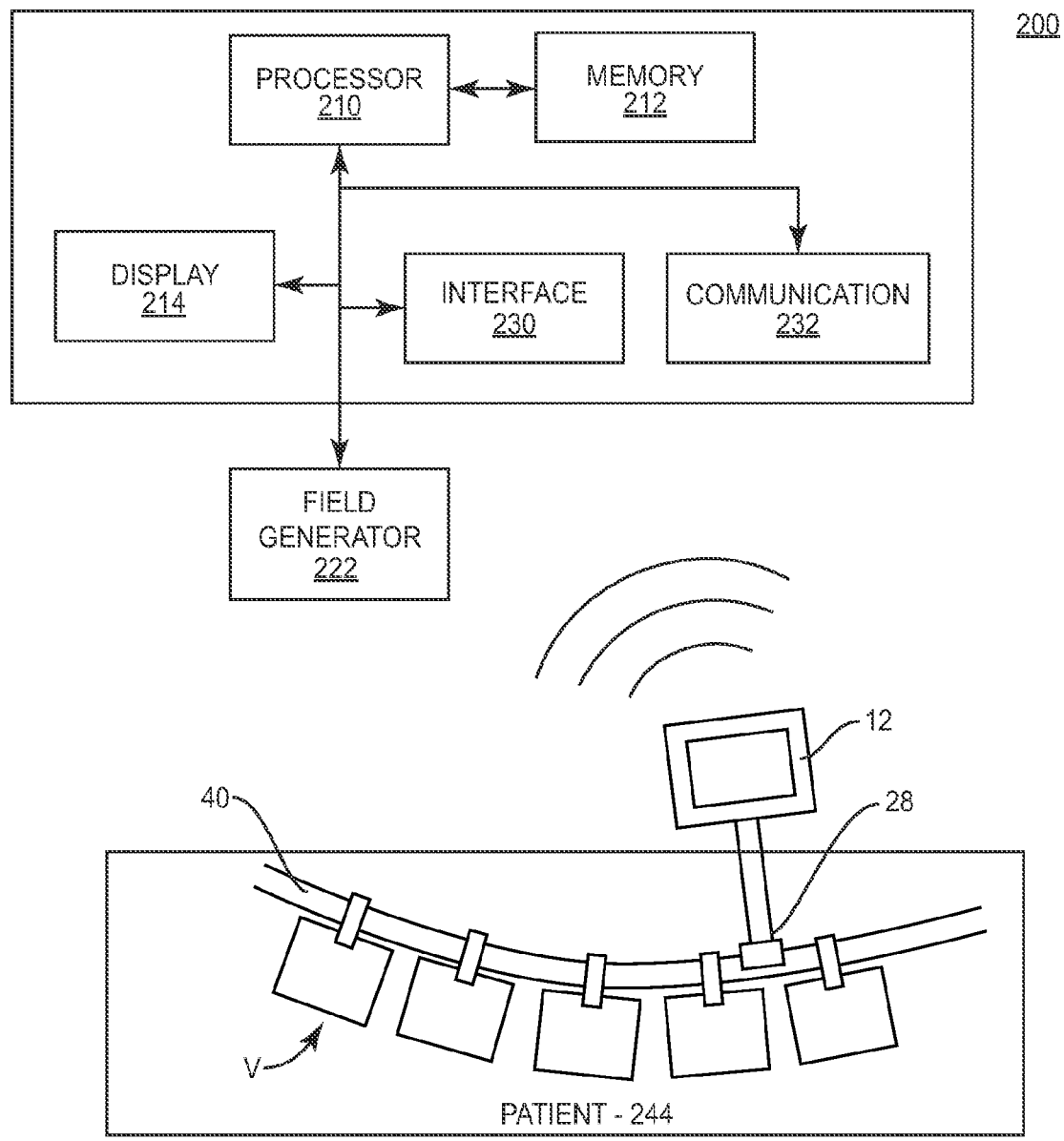
FIG. 5 is a block diagram of one embodiment of a system for measuring a spinal implant in accordance with the principles of the present disclosure.

In one embodiment, as shown in FIG. 5, device 12 includes a system 200 for assisting in measuring of geometry, such as angle or angles of rod 40. System 200 includes a processor 210 for processing data and a memory 212 for receiving angular data (and optionally positional data) representative of displacements (and position) along surgical rod 40. The data can be stored in memory 212, which can communicate with processor 210. Processor 210 may translate the data into a graphical representation on a display 214 or correlate the data in a table (e.g., angle verses position). Processor 210 receives data from device 12 and can determine angular geometries of rod 40.

Sensor 28 and processor 210 can be used to track the position device 12 in three dimensional space, relative to rod 40, relative to a reference on a patient 244, or a combination thereof. A communication module 232 may include a communication protocol with device 12 to enable communication of angle measurements from device 12. The communication link may include a wired or wireless connection. Sensor 28 may include an electromagnetic coil, such as, for example, a field generator 222 to assist in tracking end portion 20 of device 12. It is envisioned that device 12 may include an optical tracking system in place of or in addition to sensor 28, which may include one or more reflectors or light emitting diodes (LEDs). It is further envisioned that sensor 28 may be one or more radio transmitters to transmit a position signal.

System 200 may include an interface 230 with input/output devices, such as, for example, a keyboard, track ball, touch screen, mouse and/or printer. The input/output devices 230 can be used to calibrate system 200, provide graphical images or tables on display 214, control display 214, select points of reference on the graphical image, and/or perform various other functions of system 200.

Device 12 includes controls 16 to initially set and/or adjust settings relating to angular measurement or other functions of device 12. It is envisioned that controls 16 may include a variety of buttons and/or switches, such as, for example, an on/off switch, a recalibration button (to zero the device), a hold button (to hold the displayed value), or any other control corresponding to a function of device 12.

Device 12 includes a display 14 to provide a visual readout of an angle being measured by the gauge and to permit a user to interface with device 12 to initially set and/or make changes to settings, such as, for example, recalibrating the device or resetting the device.

Device 12 may include a portable energy source, such as, for example, a battery or may include a connection for an external energy source, such as, for example, a power cord connection to provide a power source for device 12 and/or components included within device 12, such as, for example, the gauge.

System 10 is configured to measure geometry of spinal implants and/or anatomy and/or position of a spinal implant and/or anatomy relative to other portions of an implant, other implants and/or anatomy. The measured geometries can include measurements based on shape, size, relative position of components of system 10, and the properties of components of system 10. For example, these measurements include angular measurements and position, and/or relative angular measurements and relative position, in any or all of a transverse, coronal and sagittal plane(s) of a body.

Figure 6:
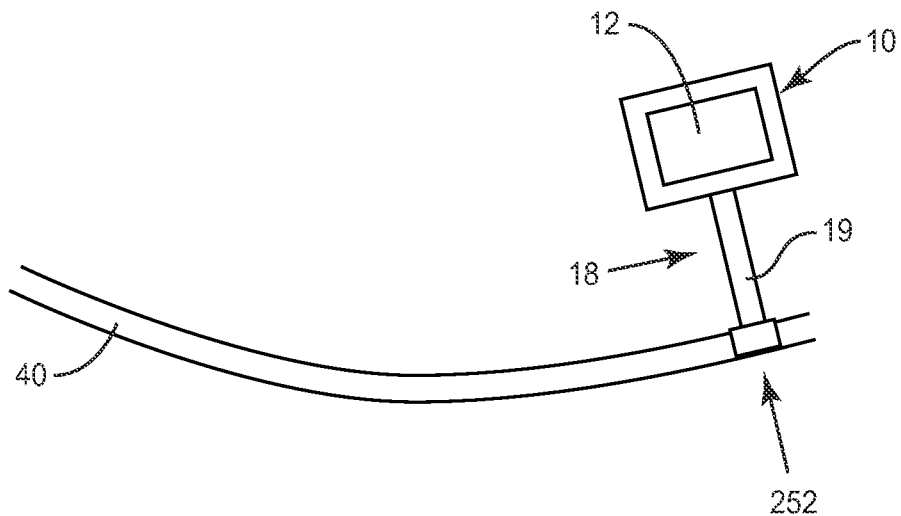
FIG. 6 is diagram illustrating measurement of a spinal implant in accordance with the principles of the present disclosure.
Figure 7:
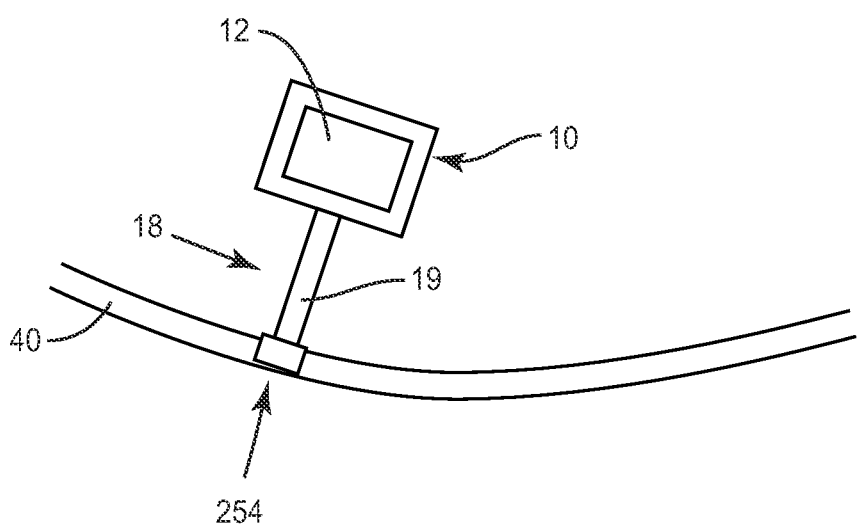
FIG. 7 is a diagram illustrating measurement of a spinal rod in accordance with the principles of the present disclosure.

In operation, as shown in FIGS. 6 and 7, spinal rod 40 is implanted with a patient and a medical practitioner measures a predetermined geometry in preparation for implanting spinal rod 40, for example, relative angle and position of portions of spinal rod 40 in the sagittal, coronal and/or transverse planes. In one embodiment, spinal rod 40 is initially configured to conform to the predetermined geometry prior to implantation of spinal rod 40 with a patient. It is envisioned that the predetermined geometry can also be input into system 200 and stored in memory 212 for use in comparing and/or verifying and/or confirming the predetermined geometry of spinal rod 40 upon implantation.

Spinal rod 40 may be mounted on a back table for measurement using system 10. Dimensions and angular geometry, such as, for example, the contour of spinal rod 40 and/or predetermined sagittal balance relative to a rod/vertebrae interface, such as, for example, rod engagement with a connector and/or a bone screw, can be measured, compared or verified prior to implantation and/or in vivo.

To measure geometry of a spinal rod 40 and/or position of spinal rod 40 relative to other portions of spinal rod 40, other implants and/or anatomy, such as, for example, vertebrae, engagement surface 26 is disposed adjacent a position 252 of spinal rod 40. Spinal rod 40 enters through the axial opening of cavity 22 and is disposed within cavity 22 at position 252, which is disposed at a first orientation, as shown in FIG. 6.

The gauge of device 12 is calibrated to a zero angle measurement at the first orientation corresponding to position 252. Engagement surface 26 is disposed adjacent a position 254 of spinal rod 40. Spinal rod 40 enters through the axial opening of cavity 22 and is disposed within cavity 22 at position 254, which is disposed at a second orientation, as shown in FIG. 7. An angle of the second orientation relative to the first orientation is measured such that the gauge determines the angle relative to the zero angle measurement. Data relating to the measured angle, for example, may be stored in system 200 or may be recorded in device 12 alone. It is envisioned that subsequent measurements and/or repositioning of engagement surface 26 with spinal rod 40 may be made relative to a plurality of positions on spinal rod 40. In one embodiment, engagement surface 26 is disposed at relative positions and orientations on an anatomy, such as, for example, vertebrae and an angle of the second orientation relative to the first orientation is measured such that the gauge determines the angle relative to the zero angle measurement.

In one embodiment, device 12 is employed to measure the angle of the second orientation relative to the first orientation to verify a selected contour of spinal rod 40 by comparing the measured angle to the selected contour. In one embodiment, the measured angle is compared to the selected contour and spinal rod 40 is adjusted to the selected contour based on the measured angle.

In one embodiment, the medical practitioner manually manipulates the vertebrae to dispose the second selected position in the second orientation. It is contemplated that the first selected position may be disposed in the second orientation in an application that the engagement surface 26 is maintained at the first selected position for an angle measurement. Device 12 is employed to measure the angle of the second orientation relative to the first orientation to verify a selected contour of spinal rod 40 by comparing the measured angle to the selected contour in situ.

In one embodiment, device 12 is employed to measure the angle of the second orientation relative to the first orientation to verify a selected sagittal balance of vertebrae relative to spinal rod 40 and a connector and/or a bone screw engaged therewith, by comparing the measured angle to the selected sagittal balance. In one embodiment, the second orientation is an apex of a scoliosis curve and vertebrae are manipulated to a selected amount of axial derotation. Device 12 is employed to measure the angle of the second orientation relative to the first orientation to verify the amount of axial derotation by comparing the measured angle to the selected amount of axial derotation. It is contemplated that the measured angle is compared to the selected sagittal balance and/or the selected amount of axial derotation, and spinal rod 40 is adjusted to the selected sagittal balance and/or the selected amount of axial derotation based on the measured angle.

Figure 8:
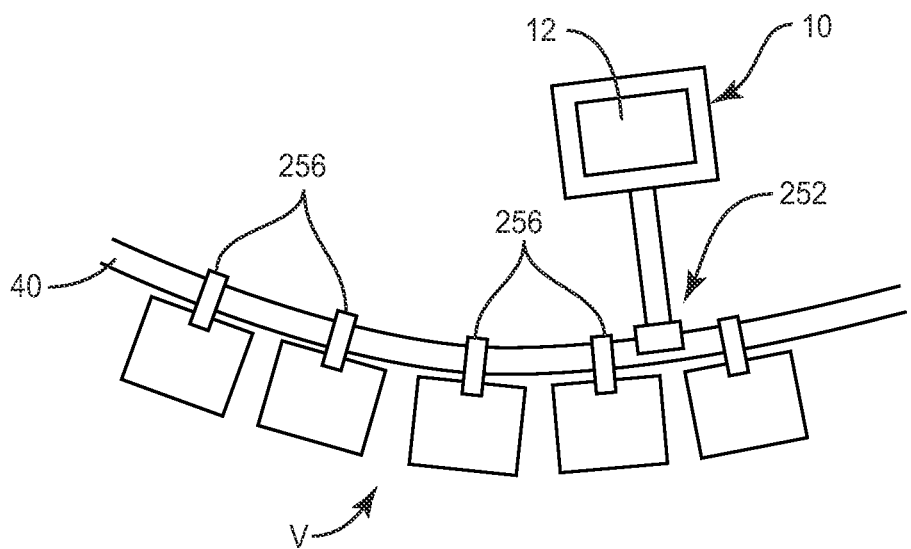
FIG. 8 is a diagram illustrating measurement of a spinal implant in accordance with the principles of the present disclosure.
Figure 9:
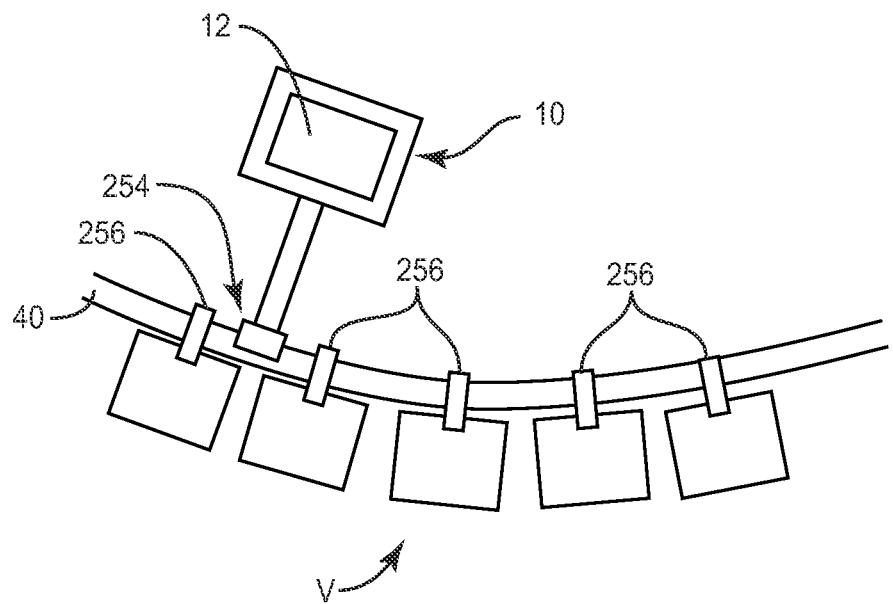
FIG. 9 is a diagram illustrating measurement of a spinal implant in accordance with the principles of the present disclosure.

In assembly, operation and use, system 10 is employed with vertebral rod system in a surgical procedure for treatment of a spinal disorder affecting a section of a spine of a patient, as discussed herein. System 10 may also be employed with other surgical procedures. In particular, system 10 including the vertebral rod system including spinal rod 40 is employed with a surgical procedure for treatment of a condition or injury of an affected section of the spine including vertebrae V, as shown in FIGS. 8 and 9.

In use, to treat the affected section of the spine, a medical practitioner obtains access to a surgical site including vertebra V in any appropriate manner, such as through incision and refraction of tissues. It is envisioned that system 10 including the vertebral rod system may be used in any existing surgical method or technique including open surgery, mini-open surgery, minimally invasive surgery and percutaneous surgical implantation, whereby the vertebrae V is accessed through a micro-incision, or sleeve that provides a protected passageway to the area. Once access to the surgical site is obtained, the particular surgical procedure is performed for treating the spinal disorder. The system 10 including the vertebral rod system is then employed to augment the surgical treatment. The vertebral rod system can be delivered or implanted as a pre-assembled device or can be assembled in situ. The vertebral rod system may be completely or partially revised, removed or replaced.

An incision is made in the body of a patient and a cutting instrument (not shown) creates a surgical pathway for implantation of the vertebral rod system including spinal rod 40 and fixation element, such as, for example, bone screws 256. A preparation instrument (not shown) can be employed to prepare tissue surfaces of vertebrae V, as well as for aspiration and irrigation of a surgical region according to the requirements of a particular surgical application.

It is envisioned that pilot holes may be made in selected vertebra of vertebrae V for receiving bone screws 256. Each bone screw 256 is inserted or otherwise engaged with a particular vertebra, according to the particular requirements of the surgical treatment. Other components may also be delivered to the surgical site along the surgical pathway(s). Spinal rod 40 is manipulated and configured in a predetermined contour, such as, for example, with regard to treatment, vertebrae orientation, sagittal balance and/or axial derotation goals, according to the requirements of a particular application. Spinal rod 40 is attached with bone screws 256 for fixation with vertebrae V. System 10 is employed to confirm, compare and/or verify the predetermined contour of spinal rod 40 with vertebrae V via angle measurement. It is contemplated that such confirmation, comparison and/or verification may be performed with system 10 prior, during or subsequent to fixation of one or all of the components of the vertebral rod system with vertebrae V, and/or may include angle measurement of vertebrae V alone.

To measure geometry and position of spinal rod 40, similar to that described, engagement surface 26 is disposed adjacent position 252. Spinal rod 40 enters through the axial opening of cavity 22 and is disposed within cavity 22 at position 252, which is disposed at a first orientation. The gauge of device 12 is calibrated to a zero angle measurement at the first orientation corresponding to position 252. Engagement surface 26 is removed from position 252 and disposed adjacent position 254. Spinal rod 40 enters through the axial opening of cavity 22 and is disposed within cavity 22 at position 254, which is disposed at a second orientation. An angle of the second orientation relative to the first orientation is measured such that the gauge determines the angle relative to the zero angle measurement.

Data relating to the measured angle is stored in system 200 and/or device 12. The measured angle is employed to confirm, compare and/or verify the predetermined contour via angle measurement. Spinal rod 40 is adjusted according to the comparison of the measured angle with the geometry parameters of the predetermined contour and/or treatment, as described. It is envisioned that a plurality of measurements, repositioning or no adjustment can be part of the procedure. It is further envisioned that the use of microsurgical and image guided technologies may be employed to access, view and repair spinal deterioration or damage, with the aid of system 10. Upon completion of the procedure, the surgical instruments and assemblies are removed and the incision is closed.

System 10 is employed with a method to confirm that spinal rod 40 is oriented and configured for disposal with vertebrae V according to a surgical application for the vertebral rod system. System 10 may also be employed in derotation applications for various spinal treatment or surgical procedures. In one embodiment, derotation includes correction of a deformity by turning or rotating the deformed structure toward a selected position. For the spine, one or a plurality of spinal rods, such as, for example, spinal rods 40 may be affixed to a spine, as described. Spinal rod 40 can be derotated and additional measurements may be made after each adjustment of spinal rod 40. In such a procedure, the spine and spinal rods of a scoliosis/kyphosis patient are rotated in increments (incremented derotation) and a measurement of the angles (e.g., axial derotation) may be made using system 10.

An amount of axial derotation of spinal rod 40 may be measured using system 10 after each adjustment or set of adjustments to verify that an appropriate amount of progress has been achieved. In one embodiment, an amount of axial derotation may be measured using system 10 by engaging an apex of a scoliosis curve to measure an amount of manual derotation applied within an axial plane.

System 10 may be employed in other surgeries or corrective procedures, such as, for example, in determining sagittal alignment or balance during a PSO. In one embodiment, PSO may be used in reconstructive spine surgery to facilitate correction of spinal deformities in the sagittal plane. Sagittal balance of a spinal column may be evaluated or verified using system 10 in vivo.

Spinal rod 40 may be characterized with the assistance of system 200. Probe 18 of system 10 may be positioned at a plurality of positions along the length of spinal rod 40 before or after implantation of spinal rod 40. Processor 210 may receive position and angular data measured respectively from sensor 28 and device 12. Processor 210 stores the data in memory 212 and can read the data from memory 212 and create a graphical or tabular representation of spinal rod 40 and display the graphical or tabular representation on display 214.

Since the data relating to spinal rod 40 is stored in memory 212, processor 210 can calculate geometries of the graphical representation of spinal rod 40 at different positions and provide comparisons. Processor 210 determines the angles between various points on the graphical representation. These points can be selected automatically by processor 210 or can be manually selected using one of input devices 230. The actual value of the angles can be displayed on display 214 so a medical practitioner can confirm that spinal rod 40 has been oriented according to the predetermined geometries. If it is determined that the angles/geometries do not match the predetermined geometries, the process can be repeated according to the requirements of a particular application.

Since the preoperative measurements may also be stored in memory 212, processor 210 can use this pre-operative data to determine whether the geometries of the spinal rod 40 are correct by comparing the geometries of the preoperative data with the geometries of the probe data. For example, angles between different points on the graphical or tabular representation can be compared with corresponding points and angles from the preoperative geometries to determine if the angles correspond. As with the selection of points, these points can be selected automatically by processor 210 or can be manually selected using one of input devices 230. It should be understood that angle and position measurements may be made by contacting the vertebrae directly. It is envisioned that such measurements may estimate relative geometries between vertebrae V and provide a point of reference for orienting spinal rod 40.

In one embodiment, the spinal implants include fixation elements employed for temporarily stabilizing at least a portion of the spinal column. The fixations elements may be removed upon the introduction of permanent stabilization components, such as, e.g., permanent rods, pins, screws etc. or upon fusing vertebrae or by employing other techniques. In addition, a surgical implant may be applied to a spinal column as a measuring tool or template. Once positioned relative to the spine or implanted with the spine, an orientation of the fixation element is achieved and locked. The temporary fixation element may be removed, and the orientation thereof may be employed as a template to select a permanent rod or implant to occupy the position on or with the spine or to provide measurement for planning treatment. In one embodiment, the spinal implant includes a connector.

Figure 2:
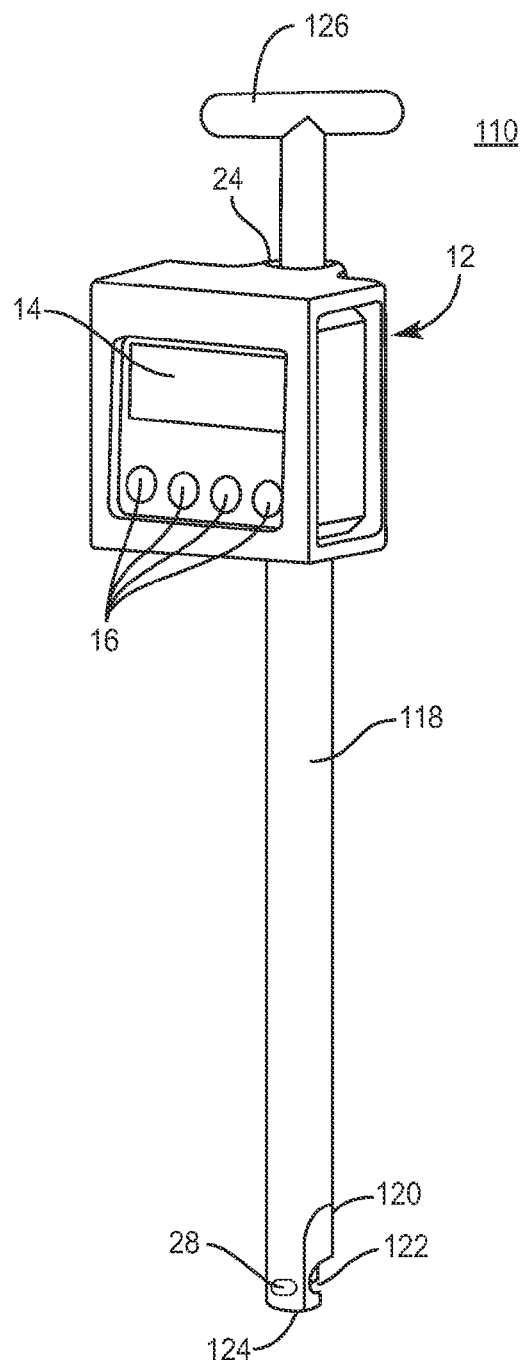
FIG. 2 is a perspective view of one embodiment of a system for measuring a spinal implant in accordance with the principles of the present disclosure.
Figure 4:
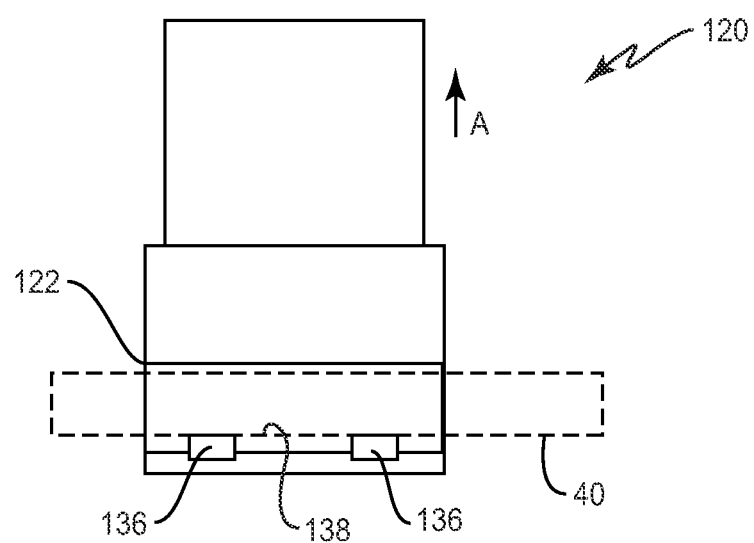
FIG. 4 is a side view of an end portion of a component of the system shown in FIG. 2.

In one embodiment, a system 110, as shown in FIGS. 2 and 4, similar to system 10 and the methods described with regard to FIGS. 1, 3 and 5-9, comprises device 12 including a gauge, described above, and aperture 24 for receiving a probe or measurement arm 118. The probe 118 is detachable and adjustably received in the aperture 24. The aperture 24 may include a set screw or other mechanism for securing a relative position of the probe 118 with respect to the device 12. The aperture 24 may be configured with a slot, a flat or other indexing structure to prevent rotation of the probe 118 about its longitudinal axis.

An end portion 120 of probe 118 includes an engagement end or surface 124, similar to surface 26 described, defining an implant cavity 122. Engagement surface 124 is parallel to a measuring plane of the gauge. Implant cavity 122 extends transversely across engagement surface 124 and includes a laterally facing opening configured to receive a spinal implant, such as, for example, a spinal rod for measuring an angle of the rod relative to another portion of the rod, a separate implant and/or the anatomy of a patient, similar to cavity 22 described.

A handle 126 is connected with probe 118 for manipulation of cavity 122 into engagement with a spinal rod for measuring an angle. Cavity 122 supports a spinal rod to permit contact surfaces 138 or engagement points 136 to grip spinal rod 40. Spinal rod 40 is retracted (e.g., using the handle 126) to cause contact with the surface 138 or with the points 136, as end portion 120 (FIG. 2) is moved in the direction of arrow "A".

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method for measuring a spinal implant, the method comprising the steps of:
   providing a device including a gauge configured to measure an angle in a measuring plane and extending to an engagement surface;
   disposing the engagement surface with a first selected position of an implant or an anatomy, the first selected position being disposed at a first orientation;
   calibrating the gauge to a zero angle measurement at the first orientation;
   disposing the engagement surface with a second selected position of the implant or the anatomy, the second selected position being disposed at a second orientation;
   measuring an angle of the second orientation relative to the first orientation such that the gauge determines the angle relative to the zero angle measurement, and
   manually manipulating the anatomy to dispose the second selected position in the second orientation; and
   verifying a selected contour of the implant or anatomy by comparing the measured angle to the selected contour in situ.

2. A method for measuring a spinal implant as recited in claim 1, wherein the implant is a spinal rod and further comprising the step of verifying a selected contour of the spinal rod by comparing the measured angle to the selected contour.

3. A method for measuring a spinal implant as recited in claim 1, wherein the implant is a spinal rod and further comprising the steps of
   implanting the spinal rod with at least one vertebra;
   verifying a selected contour of the spinal rod by comparing the measured angle to the selected contour; and
   adjusting the spinal rod to the selected contour based on the measured angle.

4. A method for measuring a spinal implant as recited in claim 1, further comprising the steps of verifying a selected sagittal balance of the anatomy relative to the implant and an anatomy interface by comparing the measured angle to the selected sagittal balance.

5. A method for measuring a spinal implant as recited in claim 1, wherein the step of providing includes an end portion having a U-shaped channel configured to receive the implant.

6. A method for measuring a spinal implant as recited in claim 5, wherein the U-shaped channel includes engagement points for engaging the implant to measure the angle.

7. A method for measuring a spinal implant as recited in claim 1, wherein the step of providing includes an end portion having an opening configured to laterally receive the implant for engaging the implant to measure the angle.

8. A method for measuring a spinal implant as recited in claim 7, wherein the opening includes engagement points for engaging the implant to measure the angle.

9. A method for measuring a spinal implant as recited in claim 1, wherein the implant is a spinal rod and further comprising the steps of:
   derotating the vertebrae a selected amount of axial derotation; and
   verifying the amount of axial derotation by comparing the measured angle to the selected amount of axial derotation.

10. A method for measuring a spinal implant as recited in claim 9, wherein the second orientation is an apex of a scoliosis curve, and further comprising the step of verifying the amount of axial derotation by comparing the measured angle to the selected amount of axial derotation.

11. A method for measuring a spinal implant as recited in claim 1, wherein the step of providing includes a position sensor mounted on the device, and further comprising the step of determining a position of the device at the second selected position in the second orientation.

12. A method for measuring a spinal implant as recited in claim 11, wherein the gauge includes an output device, and further comprising the step of establishing communication between the output device and a remote device to report the measured angle.

13. A method for measuring a spinal implant geometry, the method comprising the steps of:
   surgically treating a spine disorder including connecting a spinal rod at an interface with vertebrae in a predetermined orientation;
   providing a gauge extending to an engagement surface, the engagement surface defining an implant cavity configured for disposal of the spinal rod;
   disposing the engagement surface with a first selected position of the spinal rod such that the spinal rod is disposed in the implant cavity, the first selected position being disposed at a first orientation of the spinal rod;
   calibrating the gauge to a zero angle measurement at the first orientation;
   disposing the engagement surface with a second selected position of the spinal rod such that the spinal rod is disposed in the implant cavity, the second selected position being disposed at a second orientation of the spinal rod;
   measuring an angle of the second orientation relative to the first orientation such that the gauge determines the angle relative to the zero angle measurement;
   adjusting the spinal rod based on the comparison of the angle to the predetermined orientation;
   derotating the vertebrae a selected amount of axial derotation; and
   verifying the amount of axial derotation by comparing the measured angle to the selected amount of axial derotation.

14. A method for measuring a spinal implant rod as recited in claim 13, wherein the predetermined orientation includes a selected contour of the spinal rod and the step of comparing further includes verifying the selected contour by comparing the measured angle with the selected contour in situ.

15. A method for measuring a spinal implant as recited in claim 13, wherein the predetermined orientation includes a selected sagittal balance at the interface and the step of comparing further includes verifying the selected sagittal balance by comparing the measured angle with the selected sagittal balance.

16. A method for measuring a spinal implant as recited in claim 13, wherein the second orientation is an apex of a scoliosis curve, and further comprising the step of verifying the amount of axial derotation by comparing the measured angle to the selected amount of axial derotation.

* * * * *